United States Patent [19]

Bruckenstein et al.

[11] 4,057,478
[45] Nov. 8, 1977

[54] ELECTROCHEMICAL GAS MONITOR

[75] Inventors: Stanley Bruckenstein, Williamsville, N.Y.; William G. Sherwood, Arvada, Colo.

[73] Assignee: The United States of America as represented by the Secretary of the Interior, Washington, D.C.

[21] Appl. No.: 655,575

[22] Filed: Feb. 5, 1976

[51] Int. Cl.² .................... G01N 27/40; G01N 27/52; G01N 27/54
[52] U.S. Cl. .................. 204/195 P; 204/1 T; 204/195 R; 324/29
[58] Field of Search ............... 204/195 P, 1 K, 195 R, 204/1 P, 1 N; 324/29

[56] References Cited

U.S. PATENT DOCUMENTS

| | | | |
|---|---|---|---|
| 3,239,444 | 3/1966 | Heldenbrand | 204/195 P |
| 3,622,488 | 11/1971 | Chand et al. | 204/195 P |
| 3,685,346 | 8/1972 | Molloy | 204/195 P X |
| 3,776,832 | 12/1973 | Oswin et al. | 204/195 R |
| 3,855,096 | 12/1974 | Bergman | 204/195 P |
| 3,878,080 | 4/1975 | Luck | 204/195 P |

OTHER PUBLICATIONS

Kathleen D. N. Brummer, J. of Catalysis, vol. 9, No. 3, pp. 207-216 (1967).

*Primary Examiner*—G. L. Kaplan
*Attorney, Agent, or Firm*—Gersten Sadowsky; Donald A. Gardiner

[57] ABSTRACT

An electrochemical detection system is disclosed for measuring the amount of carbon monoxide or similar oxidizable gases present in a gas phase mixture wherein the gas phase mixture is brought into contact with a liquid electrolyte through a gas-permeable measuring electrode. The improved electrode is formed of a porous membrane of chemically-inert non-wettable material, on one side of which a layer of gold is specially deposited for contact with an electrolyte of a substantially pure aqueous solution of perchloric acid. An electrical readout system is connected to the electrode for deriving a signal from the resulting oxidation current, which corresponds to a quantitative measure of the oxidation of the gas at the electrode-electrolyte interface. In addition to the special method for forming the electrode, a method for rejuvenating it after each sample measurement is disclosed wherein the electrode is successively impressed with an oxidizing (anodic) voltage, a reducing (cathodic) voltage and a working or reading voltage in an appropriate time sequence.

9 Claims, 4 Drawing Figures

ELECTROCHEMICAL GAS MONITOR

BACKGROUND OF THE INVENTION

The present invention relates to an electrochemical apparatus and method for measuring the amount of an oxidizable gas present in gaseous mixtures such as ambient air, and more particularly to an improved carbon monoxide detection cell and electrode structure and methods for the formation and operation thereof.

Electrochemical detection cells for measuring the amount of gases such as carbon monoxide and nitrogen oxides present in a gas phase mixture are known wherein the gas phase mixture and a liquid electrolyte are brought into reactive contact through a gas-permeable measuring electrode. The electrode and the electrolyte are selected such that the particular gas diffuses through the electrode and is oxidized at the electrode-electrolyte interface at a rate proportional to its concentration in the gas phase mixture. The oxidation reaction produces an electrical current whose level is directly proportional to the reaction rate and thus to the concentration of the gas in the gas phase mixture. Such cells may be of the galvanic type wherein the measuring electrode is used with a low resistance nonpolarizable reference electrode and the reaction causes a current flow spontaneously between the two electrodes without the application of an external voltage across them. Such cells may also be of the polarographic type, which is that of the present invention, wherein a predetermined external voltage is impressed across the measuring electrode and a reference electrode, which voltage, in the absence of the gas to be detected, polarizes the system to reduce the current between the electrodes substantially to zero. When the measuring electrode is exposed to the gas to be detected, a current flows which is a function of the concentration of the detected gas in the gas phase mixture. An auxiliary electrode is usually added to the measuring and reference electrodes to complete the electrical system.

One major problem with such electrochemical cells, which is particularly severe in detecting low concentrations of carbon monoxide, is that the measuring electrode becomes gradually irreversibly poisoned, and the reaction rate accordingly varies with such poisoning. As a result, the electric current sensed is no longer indicative of the concentration of the gas in the gas phase mixture without constant recalibration.

Heretofore, it has been the common belief in the art that the use of gold for the measuring electrode in carbon monoxide monitoring cells is infeasible because such gold electrodes will not oxidize carbon monoxide, in that gold is inert to carbon monoxide, as taught, for example in U.S. Pat. No. 3,776,832, Col. 12, lines 51–57. Further, it has been understood that the use of gold with a perchloric acid electrolyte will result in rapid (within seconds) and irreversible poisoning of the electrode as taught, for example, by Brummer, K.D.N., in "A Study of the Rate of Oxidation of Carbon on Three Dispersed Electrode Systems," Journal of Catalysis 9, 207–216 (1967). However, it has been discovered that with a gold-coated electrode made in accordance with the present invention, a highly sensitive carbon monoxide monitoring cell can be produced using substantially pure perchloric acid solution as the electrolyte, and that this electrode can be rapidly rejuvenated after each sampling, by suitably varying an imposed voltage to reverse poisoning, thus obviating frequent calibrations and resulting in a cell of an indefinitely long lifetime.

SUMMARY OF THE INVENTION

The present invention involves an electrochemical detection cell for measuring the amount of an oxidizable gas, such as carbon monoxide, present in a gas phase mixture and embodying a measuring electrode, formed of a porous membrane of chemically-inert non-wettable material with a gold coating on one side, which acts as an electrocatalyst in contact with a substantially pure aqueous perchloric acid solution electrolyte and which electrode is rejuvenated after each sample measurement by the imposition of timed potential variations thereon. More particularly, the measuring electrode may be formed by coating a porous polytetrafluoroethylene (PTFE) membrane with a resinate solution or suspension containing gold and then evaporating the solution by heating at a suitable temperature to avoid damaging the PTFE thus depositing a solid gold layer. The coating and heating steps are repeated enough times to create a succession of gold layers forming a conductive coating, and the resulting structure is then heated for a substantially longer time, at the same temperature, to finally evaporate all traces of the solution or suspension which remain in the layers. It has been found that if an electrode so formed is used with a substantially pure perchloric acid solution electrolyte, the poisoning process is considerably slowed, for example, to about an half hour, as compared to a few seconds with even slightly contaminated perchloric acid solution, so that very sensitive measurements can be taken. Further, by cycling such a measuring electrode through a selected voltage profile the gold coating may be rejuvenated to the point where all or nearly all of the poisoning is removed. The voltage profile comprises: placing the gold electrode at an oxidizing potential with respect to a measuring potential for a given period of time; and then placing it at a reducing potential with respect to the measuring potential for a given period; following which it is placed at the measuring potential and a reading is taken after the passage of a suitable period of time to permit transient effects to die down. This voltage cycling may be accomplished in little more than a minute after each sampling of the gas.

In a preferred embodiment the gold-PTFE electrode is disposed at the bottom of a hollow tube immersed in an aqueous perchloric acid solution (1.0 M $HClO_4$) with the porous PTFE facing the interior of the tube and the gold coating facing and contacting the perchloric acid. The rejuvenation cycle involves oxidation at an anodic potential of 1.65 volts, close to that of oxygen evolution, for about 8 seconds; followed by reduction at a cathodic potential of about 0 volts, close to that of oxygen reduction and hydrogen evolution, for about 8 seconds; followed by establishing the potential of the electrode at its working level of 1.05 volts for a period of 48 seconds and taking the actual sample during the last 24 seconds. The potentials are on a potential scale of a saturated calomel electrode. Suitable electronic circuitry is provided which electronically compensates for temperature changes, and the device is linear in the detection range, so that calibration at a single point is sufficient. Calibration may be accomplished by feeding carbon monoxide at a known concentration to the device. As the instrument is also sensitive to other oxidizable gases such as nitrogen oxides, chemical filters may be used to oxidize or otherwise remove these gases from the gas mixture prior to letting the mixture reach the gold-PTFE electrode. Alternatively, if it is desired to detect one of the other gases, the carbon monoxide may be removed by prior filtering.

A device in accordance with the present invention will operate, with temperature compensation, in the range from 0° to 50° C and is linear in the detection range from 1 ppm to 50,000 ppm. The invention may be incorporated in a portable monitoring instrument designed for use by low-skilled personnel in field conditions, but unlike presently available instruments of this type, it will provide laboratory quality measurements, require infrequent calibration and be capable of an indefinitely long operating life in view of the rejuvenating of the electrode and the limited amount of electrolyte used up in normal use.

DETAILED DESCRIPTION OF A PREFERRED EMBODIMENT

Figure 1:
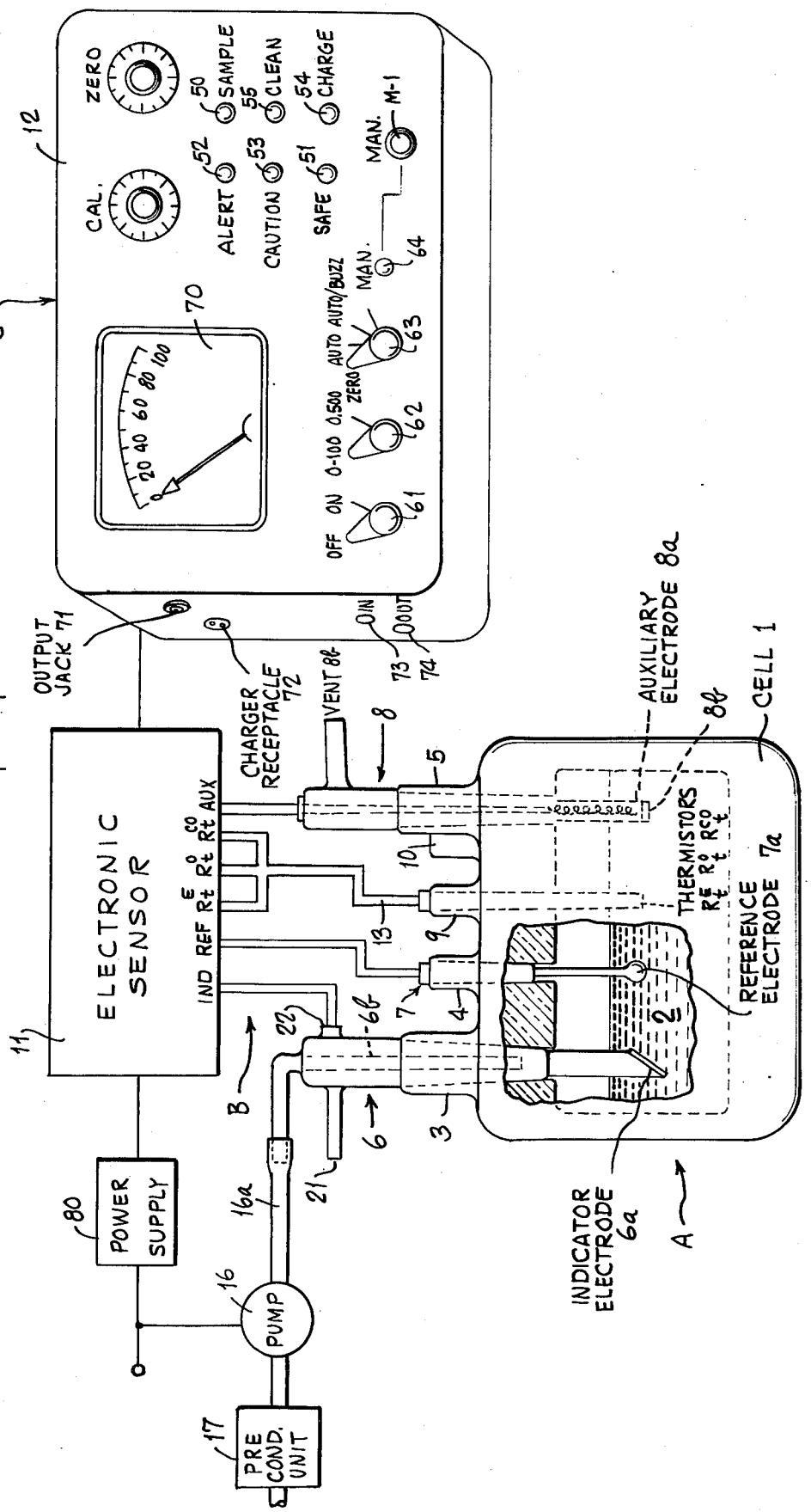
FIG. 1 is a diagrammatic representation of a monitoring apparatus constructed in accordance with the present invention.

FIG. 1 is a diagrammatic illustration of an electrochemical monitoring apparatus of the type embodying the present invention. Although the apparatus is suitable for monitoring a number of oxidizable gases and vapors, such as those containing compounds of carbon, nitrogen hydrogen, sulfur and/or oxygen, it will be particularly described as embodied in a portable carbon monoxide monitor which may be readily and effectively used under field conditions.

As shown in FIG. 1, the monitor generally comprises a detection cell and sampling system A, a sensing or measuring system B, and a display system C. The electrochemical cell may be in the form of a suitable glass cell 1, containing electrolyte 2. For the purposes of the portable monitor, the capacity of the cell may be 60 ml. The cell 1 is provided with a number of ports in its top surface for receiving appropriate sensing or measuring components and a port 10 is used for changing the electrolyte. A gas mixture to be monitored is pumped to the cell 1 by means of a pump 16 through a suitable duct 16a after being filtered and humidified in a pre-conditioning unit 17.

The sensing or measuring system B consists, firstly, of a three-electrode arrangement, that is, an indicator, a reference, and an auxiliary electrode, the components of which are respectively accommodated by suitable ports 3, 4 and 5. The indicator electrode assembly 6 contains the electrode 6a and an input tube 6b for the gas sample as will be more fully described below. The reference electrode assembly 7 contains the reference electrode 7a which may be a standard calomel electrode, but is preferably of a conventional pH or glass type. It is maintained at a constant potential with respect to the indicator electrode 6a and is of a high impedance so that no current passes therethrough. The auxiliary electrode assembly 8 contains the auxiliary electrode 8a and has provision therein for venting excess pressure in the cell 1 through vent 8b. There is a fritted glass disk 8c sealed to the end of the auxiliary electrode assembly and it prevents rapid flow of perchloric acid solution, and electrode products formed at the auxiliary electrode, between the indicator and auxiliary electrodes.

The sensing system, further, includes temperature compensation means. A suitable port 9 in the cell 1 accommodates the temperature compensating elements $R_t^E$, $R_t^O$, and $R_t^{CO}$. The assembly 13 may be in the form of a glass tube with heat conductive material disposed about the elements at least in the area which is immersed in the electrolyte. The three leads from the temperature-compensation components along with the leads from the three electrodes are all connected to the sensing electronics of the device, shown generally as 11, which completes the sensing system B.

The output of the sensing electronics is connected to the display system C which consists of a suitable display panel 12 containing a meter 70 and other operation indicators as will be more fully described below.

Figure 4:
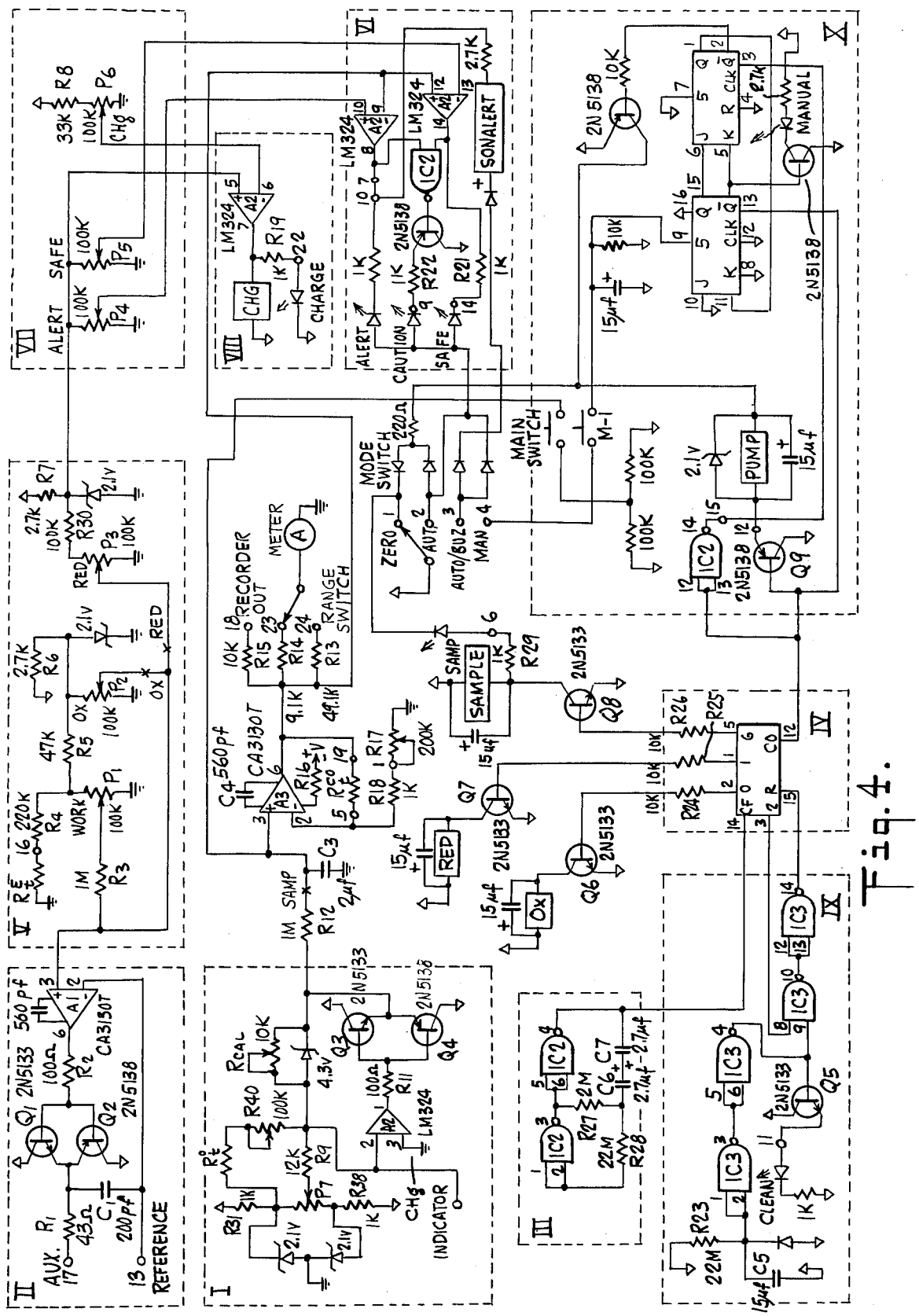
FIG. 4 is a suitable circuit schematic for use in a portable type monitor made in accordance with the present invention.

All of the components shown in FIG. 1 are preferably incorporated into a suitable portable case 14, such as obtainable from Zero Manufacturing Co., Monson, Mass., as Model #ZIP-805-C for operation as a portable monitoring unit. A complete circuit schematic comprehending the entire electronic system for this preferred portable embodiment is shown in FIG. 4.

Figure 2:
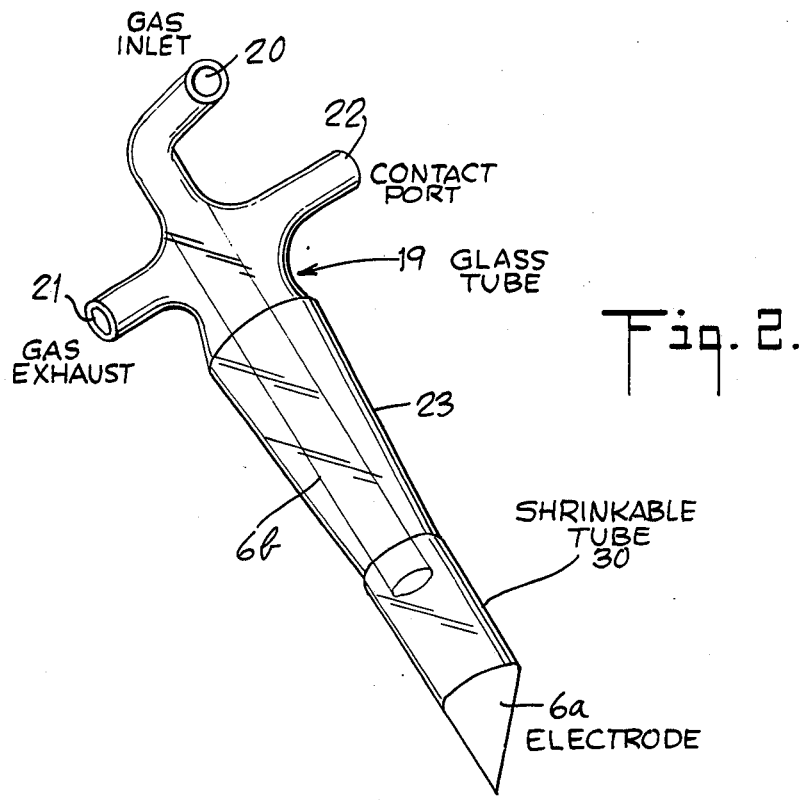
FIG. 2 is a perspective view of an indicator electrode assembly used in the monitoring apparatus of FIG. 1.

The present invention is particularly directed to the use and construction of the indicator electrode so that a preferred form of the indicator electrode assembly 6 is shown in greater detail in FIG. 2. The assembly 6 comprises a glass tube 19 having at one end a gas inlet port 20, a gas exhaust port 21, and a port 22 for the passage of the indicator electrode lead, IND. The central portion 23 of the tube 19 is tapered for a proper fit in the cell port 3. The opposite end, in contact with the electrolyte 2 in the cell, is provided with the indicator electrode 6a. The electrode is held on the end of the tube by a heat shrinkable Teflon tubing 30 as will be more fully described. The gas inlet port 20 communicates with an interior tube 6b which conducts the incoming gas mixture to be monitored from duct 16a into the lower end of the assembly 6 for contact with one side of the electrode 6a. The incoming gas mixture is pumped through tube 6b by means of the pump 16 shown in FIG. 1 and exits through the exhaust port 21. A pump unit which has been found particularly suitable for use with the preferred embodiment is the Bendix Environmental low power diaphragm pump model No. 3–75VDC-Micromotor operated at a flow rate of 500 cm³ per minute. Casing 14 may be provided with suitable sample inlet and outlet ports 73 and 74, respectively communicating with preconditioning unit 17 and exhaust port 21.

It has been found that with a monitoring cell of the type shown in FIG. 1 an indicator electrode comprising a porous membrane of chemically-inert, non-wettable of hydrophobic material, such as polytetrafluoroethylene, coated with gold in a manner in accordance with the present invention will, when used with an electrolyte consisting of a substantially pure aqueous perchloric acid solution, operate as a highly-sensitive carbon monoxide monitoring cell. The gold coating is maintained in contact with the acid electrolyte while the gas mixture is brought into contact with the porous PTFE side of the electrode. CO in the mixture will diffuse through the membrane to the electrolyte side and be oxidized into $CO_2$ at the electrode-electrolyte interface.

The resulting oxidation current is sensed by the indicator electrode and provides an indication of the reaction rate and accordingly the amount of CO present in the gas mixture. It is also contemplated that other oxidizable gases and vapors, such as those containing compounds of carbon, hydrogen, sulfur nitrogen, and/or oxygen, would be suitable for monitoring by the disclosed device.

Figure 3:
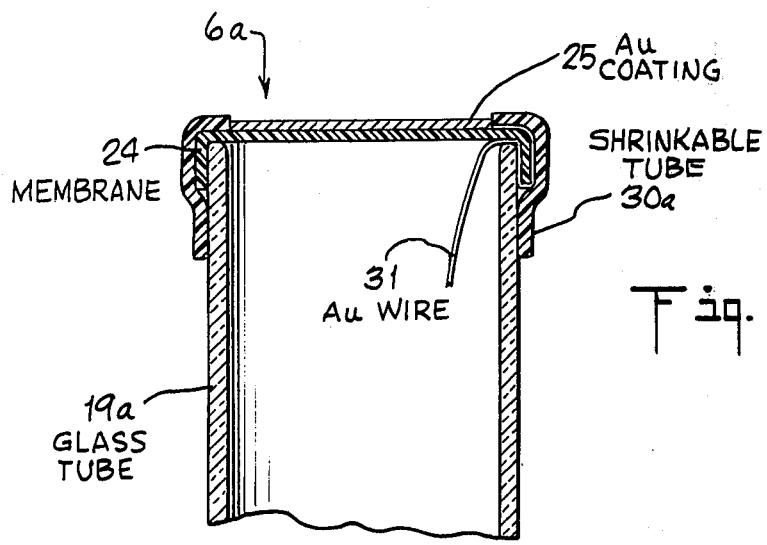
FIG. 3 is a diagrammatic view illustrating a step in the method of constructing an indicator electrode in accordance with the present invention.

In contrast to the conventional Teflon-bonded fuel cell electrodes whose construction is comparatively expensive and complex, an electrode in accordance with the present invention can be made with a simple inexpensive technique. The present indicator electrode is constructed of (1) a gas-permeable membrane of an hydrophobic or non-wettable material which is substantially chemically inert with respect to the electrolyte and the gases in the gas mixture to be monitored; and (2) a conductive gold coating disposed on one side of the membrane. PTFE has been found to be a particularly suitable material for the porous membrane, but other porous membranes or structures which are intrinsically hydrophobic or which can be treated to make them hydrophobic may be used. An organic resinate solution or suspension containing gold may be used to deposit the gold coating upon one side of the porous membrane. More particularly, in constructing the electrode, as shown in FIG. 3, a porous PTFE membrane 24, for example, of the dimensions ¾ inch × ¾ inch, having a thickness of 0.004 inch and a porosity of 82% (such as commercially obtainable under the tradename Gore-Tex from W. Gore and Associates, Maryland) may be stretched over the end of a 14 mm Pyrex glass tube 19a and fixed in place about its periphery by a suitable piece of heat-shrinkable Teflon tubing 30a. A gold wire 31, for example, of 24 gauge, is inserted between the heat-shrinkable tubing 30a and the membrane 24 prior to the shrinking process to provide an electrical contact for connection to the electrode lead. The heat-shrinkable tubing 30a may be heated using a 1500 watt heater blower for less than one minute to effect shrinking. Then two or three drops of gold resinate solution are applied to the membrane 24 so held and spread over its surface using a small brush. A suitable gold resinate solution is that manufactured by the Hanovia Liquid Gold Division of Englehard, New Jersey, under the designation No. 8300 which contains 28% gold in an organic solvent that is vaporizable at temperatures between 200° and 500° C when painted as a thin layer. Some gold powder may be added to the resinate if desired. The membrane with the resinate coating may then be held vertically and rotated at the output of the heater. Care must be taken during this step not to heat the PTFE to more than 250° C to keep it substantially below its fusing or decomposition temperature. The resinate solution should dry rapidly leaving a black film on the surface of the membrane. The black film will become, on continued heating, a gold layer which adheres well to the PTFE. Ordinarily, this single layer will prove, upon testing, not to be sufficiently conductive so that the process may be repeated a number of times, preferably three. Accordingly, after three gold resinate coats have been applied to the membrane and dried, the electrode is placed in a 240° C oven for 8 hours. This step insures complete removal of all resinate material from the surface of the membrane 24 leaving a conductive gold coating 25. Finally, the gold coating is then electrochemically cleaned and activated in perchloric acid solution for about 24 hours by potential cycling the gold coating between an anodic potential that may produce oxygen evolution and a cathodic potential that may produce hydrogen evolution and/or reduce oxygen. This procedure has been found to work with a square wave, sine wave and triangular wave potential cycle from a frequency of 1 Hertz to at least 60 Hertz. At somewhat higher frequencies electrochemical complications may interface with this electrochemical cleaning and activation step. The surface area of an electrode prepared in this manner is approximately 100 $cm^2$. The electrode 6a will exhibit less than 1 ohm resistance across its surface. It is contemplated that the gold or other electrocatalyst can also be applied to the porous, hydrophobic membrane by vacuum evaporation, sputtering, electro-deposition or the like in forming the electrode of the present invention, but the above-described process has been found to be simple, inexpensive and quite satisfactory.

The configuration of the indicator electrode may be varied, such as shown in FIGS. 1 and 2, wherein it is disposed at an angle to the vertical to permit the removal of bubbles that may form during the electrode rejuvenating process which will now be described.

Fritted glass has also been found to be a suitable material upon which a gold coating may be deposited using the gold resinate procedure. The fritted glass structure, coated with gold on one side, may be treated with a silanizing agent to produce a hydrophobic electrode structure.

It has not been appreciated by those skilled in the art that the CO limiting oxidation current in 1.0 M $HClO_4$ decays with time as the result of adsorption of the variety of impurities which may be present in the supporting electrolyte. The rate of decay depends upon the purity of the particular batch of acid used. In addition, the rate of decay increases with time as impurities are adsorbed from the ambient atmosphere. These impurities "poison" the electrooxidation process. It has been found that an appropriate electrode reactivation or "rejuvenation" scheme is possible by applying carefully controlled and timed potential programs to the indicator electrode. Depending on the potential program employed, stable CO oxidation currents can be obtained for various lengths of time. More particularly, the suitable potential sequences generally involve: (a) oxidation of the electrode for a time $t_{ox}$; (b) reduction of the electrode surface for a time, $t_r$; and (c) measurement of the CO oxidation current for a time, $t_{CO}$, at an appropriate potential. The corresponding potentials for the various times defined above are indicated as $E_{ox}$, $E_r$ and $E_{CO}$ and particular values for programs which have been found to be useful are given in Table I. Program C and D are preferred for use in a portable monitor constructed in accordance with the present invention.

TABLE I

| | INDICATOR ELECTRODE POTENTIAL SEQUENCES | | | | | |
|---|---|---|---|---|---|---|
| | OX | | RED | | LIMITING CURRENT | |
| SEQUENCE | $E_{ox}$,V | $t_{ox}$,sec. | $E_r$,V | $t_r$,sec. | $E_{CO}$,V | $t_{CO}$, sec. |
| A | 1.60 | 30 | 0.00 | 60 | 1.05 | 600 |
| B | 1.40 | 45 | 0.00 | 45 | 1.05 | 480 |
| C | 1.60 | 8 | 0.10 | 8 | 1.05 | 48 |

TABLE I-continued
INDICATOR ELECTRODE POTENTIAL SEQUENCES

| SEQUENCE | OX | | RED | | LIMITING CURRENT | |
|---|---|---|---|---|---|---|
| | $E_{ox}$,V | $t_{ox}$,sec. | $E_r$,V | $t_r$,sec. | $E_{CO}$,V | $t_{CO}$, sec. |
| D | 1.60 | 8 | 0.60 | 8 | 1.04 | 48 |

By way of understanding the significance of the data in Table I, consider sequence C. First, the potential on the indicator electrode is set at an oxidizing potential $E_{ox}$ (1.60 V vs. a Saturated Calomel Electrode) for 8 seconds. This oxidation removes the effects of the electrolyte "poisoning." A potential much larger than 1.6 volts if applied for too long may overoxidize and damage the electrode surface and thus decrease its accurate measuring ability.

The oxidized electrode is then stepped to a reducing potential $E_r$ (0.10 V vs. the SCE) for 8 seconds. The more negative or cathodic the potential is swung with respect to the oxidizing potential the faster will be the reduction process. However, caution must be exercised during reduction to avoid reducing the $O_2$ in the gas sample and producing $Cl^-$ in the electrolyte. Also the reduction time must be gauged by the time taken to oxidize the electrode. Accordingly, the 0.60 volt potential in sequence D should produce less reduction products.

Finally, the potential is stepped to a level for oxidizing CO (1.05 V vs. the SCE) for 48 seconds. The longer period is taken in this step to permit the electrode to stabilize. Potentials much larger than 1.05 volts will tend to undesirably oxidize the electrode surface and affect accurate measurement. Valid readings for the CO concentration (in the gas stream flowing over the gas phase side of the indicator electrode) can be obtained during the last 16 seconds of the limiting current cycle for sequence C and D. For sequences A and B valid readings can be obtained during the last 60 seconds.

The indicated values of $t_{CO}$ are extremely conservative, and in practice, valid readings for CO concentration can be obtained for far longer times in a laboratory situation. However, in order to guarantee that there will be no poisoning of the electrode in hostile environments, sequences C and D which rejuvenate the electrode surface every 64 seconds are suggested for the preferred portable field monitors. Portable monitors using sequence D have been found to be particularly less sensitive to physical vibration, perhaps due to the lessened production of reduction products.

Referring again to FIG. 1, the remainder of the features of construction and operation of the preferred embodiment will be discussed.

A pH or glass electrode is preferred for the reference electrode 7 since it rapidly adopts a stable potential in 1 M $HClO_4$ and its potential is unaffected by the presence of CO, air or nitrogen in keeping with the fact that it does not exhibit redox behavior. While it may introduce noise into the measured CO oxidation current as a result of its high internal impedance, appropriate filtering in the sensing electronics and grounding to the metal of the portable case may be used to remove most of the noise. Further a glass electrode eliminates the possibility of chloride contamination which may accompany the use of an SCE since the presence of $Cl^-$ significantly alters the current-time response for CO oxidation and must be avoided if accurate results are to be obtained.

In selecting the auxiliary electrode 8a special care should be taken to avoid the use of a material at which "harmful" intermediates are generated. For example, the use of platinum is undesirable since over a long term deposition of platinum on the gold indicator electrode 6a may occur, changing its behavior to that of a platinum electrode. A tightly coiled gold wire is preferred for the auxiliary electrode 8a which should have sufficient area to keep the cell resistance low enough to provide the necessary current requirements during potential sequencing.

A power supply 80 for the portable monitor is preferably a set of rechargeable batteries, for example, 10 1.2 ampere hour Ni-Cd cells connected in series. A charger receptacle 72 is provided in case 14 to facilitate recharging. Provision may also be made for operation directly from an AC line during charging.

In the preferred embodiment a monitor for use under field conditions should be compensated for temperature effects. Firstly, the potential that must be applied with respect to the reference electrode in order to be at the optimum potential for measuring the limiting CO oxidation current is a function of temperature so that (a) the temperature coefficient of the potential of the reference electrode and (b) the temperature coefficient of the potential for formation of gold oxide must be considered. The temperature compensation should adjust the potential of the gold indicator electrode so as not to form gold oxide at the temperatures of interest and still remain in the limiting current region. The thermistor $R_t^E$ is provided for this compensation in combination with its associated circuit elements in the circuit shown in FIG. 4.

Next, the temperature coefficient of the response of the indicator electrode in the absence of CO (the residual current response) must be considered. The thermistor $R_t^O$ is provided for temperature compensation in correcting the instrument to "zero."

Finally, the temperature coefficient of the response in the presence of CO (the sensitivity) must be considered. The thermistor $R_t^{CO}$ is used for this compensation.

The operation of these three thermistors, as well as the remainder of the circuitry disclosed in FIG. 4 will be substantially self-explanatory to those skilled in the art so that a detailed discussion of the entire circuit operation will not be presented herein. However, in general, it will be seen that the portions of the circuit enclosed in blocks I and II of FIG. 4 provide respectively the current measuring function and the potential control function for the electrochemical cell. The temperature dependent background current is compensated with the thermister $R_t^O$, in block I, which has a value of 10 K ohms (25° C). One side of the thermistor $R_t^O$ is connected to variable resistor 40, and the other side is connected to the 2.1 volt side of 1 K ohm zero adjustment potentiometer P7. One end of potentiometer P7 is connected to the negative battery voltage through resistor R38, while the other end is connected to the positive battery voltage through resistor R31. The 2.1 volt Zener diodes in parallel with potentiometer P7 ensure a constant offset voltage over the entire range of usable battery power supply voltages. Resistor R9 between the wiper of potentiometer P7 and the summing point of amplifier A2 provides for the injection of a current opposite in sign and equal in magnitude to the sum of the background current and the current through thermistor $R_t^O$.

The circuitry enclosed in blocks III and IV provide the timing and control functions. Block III contains an astable multivibrator which produces pulses at, for example, 8 second intervals. These pulses are fed into a binary counter contained in block IV, the outputs of which are used to control: (1) the rejuvenating potential program imposed on the indicator electrode 6a; (2) the air sampling pump 16; and (3) Follow-Hold amplifier A3. Relays "OX" and "Red" are used to perform the potential program. Output 12 of the counter and transistor Q9 control the pump operation, while the "Sample" relay controls amplifier A3.

For example, when using potential sequence C, during the first 8 seconds of the timing program ($t_s = 0$ to $t_s = 8$) the indicator electrode is controlled at $E_{ox}$. During the next 8 seconds ($t_s = 8$ to $t_s = 16$) the indicator electrode potential is held at $E_r$. For the remaining time ($t_s = 16$ to $t_s = 64$) the electrode is maintained at the potential required to sense (oxidize) CO, $E_{CO}$. At $t_s = 32$ the air sampling pump 16 is switched on, and it remains on for the rest of the cycle period (until $t_s = 64$). The 50% duty cycle for the pump minimizes power consumption in the portable monitor. This feature would not be necessary in an AC powered device such as would be used in a laboratory or other stationary installation.

After the first 32 seconds of the $E_{CO}$ timing period, the Follow-Hold amplifier A3 indicates the CO level being sensed for 8 seconds ($t_s = 48$ to $t_s = 56$). At $t_s = 56$ the meter reading indicating the CO level is stored and, after 8 more seconds, the entire cycle is repeated.

Zero set and span calibration are possible only in the time interval $t_s = 48$ to $t_s = 56$, i.e., when the Follow-Hold amplifier A3 is in the follow mode; this state may be indicated by a green LED on the display panel.

The appropriate potentials and the temperature compensation previously described for $E_{CO}$ are obtained from $V_{REF}^-$ and $V_{Ref}^+$ (−2.1 and +2.1, respectively) and a resistor network shown in block V. Pin 16 is connected to one side of thermistor $R_t^E$ which has a value of 100 K ohm (25° C) and the other side of which is connected to ground.

A resistor network at the output of the Follow-Hold amplifier, A3, performs a number of functions. Scaling for the meter may be accomplished by switching between resistors $R_{14}$ and $R_{13}$. The range 0–500 ppm is selected by contacting pin 23, and the range 0–100 ppm by contacting pin 24 using knob 62 on panel 12. The recorder output (10 mV/ppm CO) is selected by contacting pin 18. The temperature compensation for the CO sensitivity is achieved with thermistor $R_t^{CO}$, which has a value of 100 K ohm (25° C) and which controls the gain of amplifier A3 as connected in a feedback position between pins 5 and 19.

Audio and visual warning comparators in block VI are also connected to the output of amplifier A3. These comparators can be set from a resistor network in block VII to provide: (1) a "SAFE" indication, in the form of a green LED 51, which is set for levels below 40 ppm CO; (2) an "ALERT" indication, in the form of a red LED 52 and Sonalert beeper, which is set for levels above 60 ppm CO; and (3) a "CAUTION" indication for levels between "SAFE" and "ALERT" levels in the form of a yellow LED 53. The LED indicators are shown on panel 12 in FIG. 1.

A comparator in block VIII switches if the battery voltage becomes too low for accurate operation. When this condition exists, the "CHARGE" indicator, in the form of a red LED 54 on panel 12, lights and the porous gold electrode is disconnected by means of the "Chg" relay to prevent CO response changes that can occur if the indicator electrode is exposed to unusual potentials. This feature also prevents erroneous indication of the CO level which can occur at low battery voltages.

The circuitry in block IX times and controls a continuous oxidation-reduction sequence (8 seconds each), with no $E_{CO}$ step, for the first three minutes after turning on the monitor main on/off switch 61. This sequence may be indicated by a red LED 55 on the display panel 12 and may be included to rejuvenate the electrode, a step that may be required if the power has been off. Under storage conditions, there is no assurance that the indicator electrode has not been poisoned accidentally and this initial procedure avoids problems associated with "power-off" storage.

Circuits in block X provide for automatic or manual initiation of the sampling process. This circuitry allows the operator, after selecting the Manual mode of operation using knob 63, to obtain a CO reading by pressing Push Button M-1 and does not interrupt the potential control sequence. It merely resets the meter reading below zero and lights the "MANUAL" LED indicator on display panel 12. At $t_s = 64$ this LED switches off, and a valid CO reading is displayed for 48 seconds on the meter 70. The meter reading then returns to zero until another manual cycle is initiated. The manual mode may be included to conserve power where continuous automatic operation is not necessary, since the level indicating lights and the pump remain off unless the manual cycle is initiated.

It should also be noted that a monitor in accordance with the present invention can be used to alternatively monitor NO and $NO_2$ if desired. The particular gas to be monitored may be readily selected by merely prefiltering the unwanted gases in the preconditioning unit 17 shown in FIG. 1. For use with the CO monitor, a particularly suitable filter for removing NO and $NO_2$ from the gas stream has been found to be that commercially obtainable as Purafil Odoroxidant from E. H. Burroughs Co., Chamblee, Georgia. A suitable humidifier may also be included in the preconditioning unit. Remote monitoring may also be accomplished by connecting a suitable pickup to an output jack 71 in casing 14.

It will be seen that an electrochemical gas monitoring device is provided utilizing an improved electrode stucture comprising a porous membrane of a chemically-inert and hydrophobic material on one side of which an electrocatalyst in the form of a conductive porous gold coating has been applied, which coating is disposed in contact with an electrolyte of a substantially pure aqueous perchloric acid solution, and which electrode may be rejuvenated after each sampling of a gas mixture by the successive imposition of an oxidizing potential, a reducing potential and a measuring potential in an appropriate time sequence. Extended rejuvenation cycling may permit the incorporation of the monitor in chromatographic detection apparatus and its use with a number of oxidizable gases. It should be understood that the term oxidizable gases as used herein is intended to comprehend CO, NO, $NO_2$, $SO_2$, methanol, ethanol, acetylene, ethylene and other oxidizable compounds containing carbon, nitrogen, sulfur, hydrogen, and/or oxygen, and to refer to any species present in the gas phase mixture sampled although found in the liquid or solid state in its pure form.

We claim:

1. An apparatus for quantitatively detecting a selected oxidizable gas present in a gas phase mixture comprising:
   means for providing a supply of electrolyte comprising a substantially pure aqueous perchloric acid solution;
   a porous electrode comprising an hydrophobic material which is chemically inert to said electrolyte and said gas phase mixture and having a first side comprising gold electrocatalyst means for contacting said electrolyte at an interface and a second side for contacting said gas phase mixture, said electrode allowing at least said selected oxidizable gas present in said gas phase mixture to diffuse from the mixture to said electrocatalyst-electrolyte interface;
   means for supplying said gas phase mixture to said second side of said electrode;
   means for removing non-selected oxidizable gases which are capable of diffusing to said electrocatalyst-electrolyte interface from said gas phase mixture prior to it being supplied to said second side; and
   means electrically connected to said electrode for deriving a signal corresponding to a quantitative measure of the oxidation of the selected oxidizable gas at said interface.

2. Apparatus as in claim 1 wherein said hydrophobic material comprises a porous membrane and said gold electrocatalyst means comprises a gold coating deposited on said membrane.

3. Apparatus as in claim 2 wherein said membrane comprises polytetrafluoroethylene.

4. Apparatus as in claim 1 further comprising means for rejuvenating said electrode.

5. Apparatus as in claim 4 wherein said means for deriving a signal comprises:
   a reference electrode and an auxiliary electrode, and wherein said rejuvenating means comprises:
      means for placing said porous electrode at a selected oxidizing potential for a selected oxidizing time period using said reference electrode and said auxiliary electrode; and
      means for placing said porous electrode at a selected reducing potential for a comparable reducing time period using said reference electrode and said auxiliary electrode.

6. A carbon monoxide monitor for quantitatively measuring carbon monoxide present in a gas phase mixture comprising:
   an electrolyte of a substantially pure aqueous perchloric acid solution;
   a porous electrode having one side in contact with said electrolyte to form an oxidizing interface and the other side in contact with said gas phase mixture, said electrode comprising:
      a membrane of an hydrophobic material which is chemically inert with respect to said electrolyte and said gas phase mixture and permeable to carbon monoxide; and
      a conductive gold coating adhered to one side of said membrane, which side is the side of said electrode forming said oxidizing interface, said coating permitting carbon monoxide to diffuse therethrough to said interface;
   means for supplying said gas phase mixture to said other side of said electrode; and
   means electrically connected to said electrode for deriving a signal corresponding to a quantitative measure of the amount of oxidation of carbon monoxide at said interface.

7. A monitor as in claim 6 further comprising an auxiliary electrode comprising a coil of gold wire.

8. A monitor as in claim 6 further comprising means for temperature compensation.

9. A carbon monoxide monitor for quantitatively measuring carbon monoxide present in a gas phase mixture comprising:
   an electrolyte of a substantially pure aqueous perchloric acid solution;
   a porous electrode having one side in contact with said electrolyte to form an oxidizing interface and the other side in contact with said gas phase mixture, said electrode comprising;
      a membrane of an hydrophobic material which is chemically inert with respect to said electrolyte and said gas phase mixture and permeable to carbon monoxide; and
      a conductive gold coating adhered to one side of said membrane, which side is the side of said electrode forming said oxidizing interface, said coating permitting carbon monoxide to diffuse therethrough to said interface;
   means for supplying said gas phase mixture to said other side of said electrode;
   a glass reference electrode; and means electrically connected to said porous electrode and said reference electrode for deriving a signal corresponding to a quantitative measure of the amount of oxidation of carbon monoxide at said interface.

* * * * *